United States Patent
Ye et al.

(10) Patent No.: US 11,466,566 B2
(45) Date of Patent: Oct. 11, 2022

(54) REAL-TIME MONITOR AND CONTROL OF ACTIVE CLAY IN WATER-BASED DRILLING FLUIDS

(71) Applicant: Halliburton Energy Services, Inc., Houston, TX (US)

(72) Inventors: Xiangnan Ye, Cypress, TX (US); Dale E. Jamison, Humble, TX (US)

(73) Assignee: Halliburton Energy Services, Inc., Houston, TX (US)

(*) Notice: Subject to any disclaimer, the term of this patent is extended or adjusted under 35 U.S.C. 154(b) by 557 days.

(21) Appl. No.: 16/613,786

(22) PCT Filed: Dec. 27, 2018

(86) PCT No.: PCT/US2018/067708
§ 371 (c)(1),
(2) Date: Nov. 14, 2019

(87) PCT Pub. No.: WO2020/139352
PCT Pub. Date: Jul. 2, 2020

(65) Prior Publication Data
US 2020/0378252 A1   Dec. 3, 2020

(51) Int. Cl.
*E21B 49/08* (2006.01)
*C09K 8/22* (2006.01)
(Continued)

(52) U.S. Cl.
CPC .............. *E21B 49/087* (2013.01); *C09K 8/22* (2013.01); *E21B 21/062* (2013.01);
(Continued)

(58) Field of Classification Search
CPC .... E21B 49/005; E21B 49/087; E21B 21/062; G01N 31/164; G01N 33/2823; C09K 8/22; G16C 20/30
See application file for complete search history.

(56) References Cited

U.S. PATENT DOCUMENTS 3,605,501 A * 9/1971 Chenevert .......... G01N 15/0893
73/866
4,136,739 A * 1/1979 Salathiel .................. C09K 8/72
166/300
(Continued)

FOREIGN PATENT DOCUMENTS

| WO | 2015023185 | 2/2015 |
| WO | 2017112712 | 6/2017 |
| WO | 2018038717 | 3/2018 |

OTHER PUBLICATIONS

ISRWO International Search Report and Written Opinion for PCT/US2018/067708 dated Sep. 25, 2019.
(Continued)

*Primary Examiner* — John Fitzgerald
(74) *Attorney, Agent, or Firm* — Tenley Krueger; C. Tumey Law Group PLLC (57) ABSTRACT

Systems and methods for this disclosure describe systems and methods that are directed to monitoring active clay in water-based drilling fluid may be provided. A method for monitoring active clay concentration while drilling may be provided. The method may include providing a sample of water-based drilling fluid. The method may further include adding methylene blue to the sample in a methylene blue titration. The method may further include performing an impedance measurement on the sample during the methylene blue titration. The method may further include determining an endpoint of the methylene blue titration using a phase angle measurement from the impedance measurement. The method may further include correlating the endpoint to the active clay concentration of the sample. The method may further include determining a treatment for the water-based drilling fluid based on the active clay concentration.

20 Claims, 9 Drawing Sheets

(51) Int. Cl.
*E21B 21/06* (2006.01)
*G01N 31/16* (2006.01)
*E21B 49/00* (2006.01)
*G16C 20/30* (2019.01)
*G01N 33/28* (2006.01)

(52) U.S. Cl.
CPC ........... *E21B 49/005* (2013.01); *G01N 31/16* (2013.01); *G01N 31/164* (2013.01); *G16C 20/30* (2019.02); *G01N 33/2823* (2013.01)

(56) References Cited

U.S. PATENT DOCUMENTS

| | | | | |
|---|---|---|---|---|
| 4,452,900 A * | 6/1984 | Yong | ...................... | G01N 33/42 436/163 |
| 4,904,603 A | 2/1990 | Jones et al. | | |
| 9,399,911 B2 | 7/2016 | Mikhailov et al. | | |
| 10,718,749 B2 * | 7/2020 | Deng | .................... | G01N 1/4022 |
| 11,131,659 B2 * | 9/2021 | Ye | ....................... | G01N 33/2835 |
| 11,143,024 B2 * | 10/2021 | Ye | ........................ | G01N 27/026 |
| 11,293,239 B2 * | 4/2022 | Ye | ........................ | E21B 21/062 |
| 2006/0214671 A1 | 9/2006 | Wooton et al. | | |
| 2011/0281370 A1 * | 11/2011 | McMennamy | ......... | G01N 21/79 422/62 |
| 2018/0080917 A1 * | 3/2018 | Deng | .................... | G01N 30/88 |
| 2020/0278337 A1 * | 9/2020 | Deng | ................... | G01N 33/442 |
| 2021/0404271 A1 * | 12/2021 | Ye | ........................ | G01N 27/221 |
| 2022/0050050 A1 * | 2/2022 | Sun | ........................ | G01N 1/2035 |

OTHER PUBLICATIONS

Leung, P. K., & Steig, R. P. (1992). Dielectric Constant Measurements: A New, Rapid Method to Characterize Shale at the Wellsite. SPE/IADC Drilling Conference.

* cited by examiner

REAL-TIME MONITOR AND CONTROL OF ACTIVE CLAY IN WATER-BASED DRILLING FLUIDS

BACKGROUND

During the drilling of a wellbore into a subterranean formation, a drilling fluid, also referred to as a drilling mud, may be continuously circulated from the well surface down to the bottom of the wellbore being drilled and back to the well surface again. The drilling fluid may include a mixture of water, oil, additives (e.g., viscosifiers, weighting materials, emulsifying surfactants, and the like), and combinations thereof, to impart certain properties to the drilling fluid to satisfy different drilling requirements.

The formation materials encountered while drilling into a subterranean formation can vary widely depending on the location and depth of the desired reservoir. One commonly encountered material is shale, which is generally included of various clays. Clay hydration, commonly seen when ordinary water-based drilling fluids are used in water-sensitive formations, can be a significant cause of wellbore instability. Further, the clays forming the shales also tend to adhere to the drill bit or to the bottomhole assembly, severely impairing the rate of penetration during drilling. In some worst case scenarios, failure to remove hydratable clay from the wellbore can lead to gumbo attacks, packing off, lost circulation, and/or stuck pipe.

To address problems associated with clay hydration, clay inhibitors may be included in the drilling fluid. Clay inhibitors may be included, for example, to prevent the migration or swelling of clay particles in reaction to a water-based drilling fluid. The efficacy of the clay inhibitors in the drilling fluid may be monitored, for example, by monitoring the amount of active clays in the drilling fluid. One technique for monitoring the concentration of active clays is the methylene blue titration, as described in API 13B-1, $4^{th}$ edition, dated March 2009. Other tests have also been developed that use dielectric constant measurements to characterize shale at the wellsite. However, the sample preparation for these techniques can be complex, requiring various steps of washing and drying processes.

BRIEF DESCRIPTION OF THE DRAWINGS

The features and advantages of certain embodiments will be more readily appreciated when considered in conjunction with the accompanying figures. The figures are not to be construed as limiting any of the preferred embodiments.

DETAILED DESCRIPTION

The present disclosure relates to drilling operations and, more particularly, embodiments disclosed herein are directed to monitoring active clay in water-based drilling fluid. As will be discussed in more detail below, embodiments may use an electric method to monitor active clay content in a drilling fluid and then determine amount of clay inhibitor needed for clay stabilization.

Embodiments may include determining methylene blue titration endpoint by using a phase angle measurement of the drilling fluid. By way of example, the phase angle may be measured during the methylene blue titration and used in determining the methylene blue titration endpoint. By using the phase angle measurement, the methylene blue titration endpoint may be determined with requiring full titration, thus potentially eliminating the time consuming process and potentially systematic errors that may be involved with methylene blue titration. The systems and methods may be used to monitor the active clay content of drilling fluid in a mud pit, on a rig, in a mud plant, in a laboratory, or at any other suitable location. In some embodiments, the systems and methods may be implemented in real-time during drilling so that a clay inhibitor can be added as needed to the drilling fluid. In some embodiments, the systems and methods may be automated so that active clay content of the drilling fluid may be monitored and corrective action can be taken (e.g., addition of clay inhibitor) as an automatic process.

The systems and methods may be used for monitoring the active clay content of any suitable water-based drilling fluid. In contrast to oil-based drilling fluids (i.e., water-in-oil or invert emulsions) with an oil continuous phase, the continuous phase of a water-based drilling fluid is the aqueous fluid, which is also the major component of the water-based drilling fluid by volume. The aqueous fluid may be from any source provided that it does not contain an excess of compounds that may undesirably affect other components in the treatment fluid. The aqueous fluid may include water. The water may be fresh water or salt water. Salt water may generally include one or more dissolved salts therein and may be saturated or unsaturated as desired for a particular application. Seawater or brines may be suitable for use in some applications. Brines in the treatment fluid may include a brine or a combination of brines. Suitable brines may be saturated or unsaturated as desired for a particular application. One or more salts may be added to water to provide a brine that includes the dissolved salt and the water. Suitable dissolved salts may include monovalent and divalent salts. Mixtures of monovalent, divalent, and trivalent salts may also be used. Suitable monovalent salts may include, but are not limited to, sodium chloride, potassium chloride, sodium bromide, potassium bromide, potassium chloride, potassium formate cesium formate, potassium formate, and mixtures thereof among others. Suitable divalent salts may include, but are not limited to, calcium bromide, zinc bromide, calcium chloride, and mixtures thereof. In an embodiment, the brine may include calcium bromide, and/or any combinations thereof. In a non-limiting example, one salt may be used to prepare the brine. In another embodiment, multiple salts may be used to prepare the brine. Specific examples of suitable brines may include a calcium bromide brine, a combination thereof. In some examples, the brine may be free or essentially free of zinc and cesium formate. The brine may be provided in any amount or concentration such as unsaturated, saturated, supersaturated, and saturated with additional solids. The brine may be present in the treatment fluid in any suitable amount. Further, the aqueous fluid may be present in an amount sufficient to form a pumpable fluid, including, but not limited to, an amount ranging from about 50% to about 90%, or about 50% to about 60%, or about 70% to about 80% based on a total weight of the water-based drilling fluid. With the benefit of this disclosure one of ordinary skill in the art should recognize the appropriate amount of water for a chosen application.

In addition, a weighting agent may be included in the water-based drilling fluid. Weighting agents are typically particulate materials with a high-specific gravity. As used herein, the term "high-specific gravity" refers to a material having a specific gravity greater than 2.6. Examples of suitable weighting agents may include, but are not limited to, barite, hematite, ilmentite, manganese tetraoxide, galena, calcium carbonate, and combinations thereof. The weighting agent may be present in the drilling fluid in an amount sufficient for a particular application. For example, the weighting agent may be included in the water-based drilling fluid to provide a particular density. Suitable amounts of the weighting agent may include, but are not limited to, the weighting agent present in the water-based drilling fluid in an amount up to about 50% by volume of the drilling fluid (vol %) (e.g., about 5 vol %, about 15 vol %, about 20 vol %, about 25 vol %, about 30 vol %, about 35 vol %, about 40 vol %, about 45 vol %, etc.) For example, the weighting agent may be present in the water-based drilling fluid in an amount ranging from of about 5 vol % to about 50 vol %, about 10 vol % to about 40 vol %, or about 20 vol % to about 30 vol % One of ordinary skill in the art with the benefit of this disclosure should recognize the appropriate type and amount of the weighting agent for a chosen application.

Water-based drilling fluids may further include a clay inhibitor. Clay inhibitors are typically chemical additives included in water-based drilling fluid to prevent and/or reduce migration or swelling of clays in reaction to the water-based drilling fluid. Examples of suitable clay inhibitors may include, but are not limited to, a polymer, such as a nonionic polymer (e.g., a nonionic polyacrylamide, alternatively, a low molecular weight nonionic polyacrylamide, or a high molecular weight nonionic polyacrylamide. As used herein, a low molecular weight nonionic polyacrylamide refers to a polyacrylamide with a molecular weight of less than two million, and a high molecular weight nonionic polyacrylamide refers to a polyacrylamide with a molecular weight of between 14 million to 16 million. In some embodiments, the clay inhibitor may include polymers derived from heterocyclic compounds further including nitrogen. In an embodiment, the polymers may or may not be crosslinked, alternatively, the polymers are crosslinked.

In an embodiment, the clay inhibitor may include a polymeric heterocyclic nitrogen-containing compound present in an amount sufficient to inhibit degradation of shale in the subterranean formation. In one embodiment, the heterocyclic nitrogen-containing compound includes straight chain polyvinyl pyrrolidone. In another embodiment, the heterocyclic nitrogen-containing compound includes crosslinked polyvinyl pyrrolidone.

The clay inhibitor may be used in any suitable amount to provide a desired level of clay inhibition for a particular application. For example, the clay inhibitor may be present in the water-based drilling fluid in an amount of about 0.01 wt. % to about 10 wt. % based on a total weight of the water based drilling fluid, alternatively about 0.1 wt. % to about 5 wt. % based on a total weight of the water based drilling fluid, or about 0.5 wt. % to about 3 wt. % based on a total weight of the water based drilling fluid. Additional clay inhibitor may be added to the water-based drilling fluid during operations, as needed for a particular application. As will be discussed in more detail below, embodiments may include monitoring active clay in the water-based drilling fluid and taking corrective action by addition of additional clay inhibitor as needed.

Water-based drilling fluids may further include a clay. Clays may be included in the water-based drilling fluids, for example, to provide a viscosity increase to, among other things, increase carrying capacity and reduce fluid loss. Examples of suitable clays may include, but are not limited to, bentonite, hectorite, kaolinite, attapulgite, and sepiolite. The clay may be present in any suitable amount for a particular application. For example, the clay may be present in the water-based drilling fluid in an amount in a range of about 0.01 wt. % to about 20 wt. % based on a total weight of the water-based drilling fluid. Alternatively, the clay may be present in an amount of about 0.1 wt. % to about 15 wt. % by weight or about 1 wt. % to about 10 wt. % by weight based on a total weight of the water-based drilling fluid. One of ordinary skill in the an with the benefit of this disclosure should be able to select the appropriate type and amount of clay for a particular application.

Water-based drilling fluid may further include a solid bridging agent. Bridging agents typically include sized solid particulate capable of forming a bridge across the pore throat or fractures of an exposed rock thereby building a filter cake which may aid in preventing loss of whole mud or excessive filtrate may be used. Solid bridging agent may include, without limitation, soluble particulars, such as, acid-soluble particulates. Examples of suitable solid bridging agents may include, but are not limited to, calcium carbonate, salt particulates, iron carbonate, zinc carbonate, polylactic acid, wax particulates, magnesium carbonate, magnesium oxide, manganese tetraoxide, graphitic materials and combinations thereof. The solid bridging agent may include any particle size distribution as desired for a particular application. In certain embodiments, the solid bridging agent may have a mean particle size in a range of from about 1 micron to about 200 microns as defined by ASTM methods. The mean particle size corresponds to d50 values as measured by particle size analyzers such as those manufactured by Malvern Instruments, Worcestershire, United Kingdom. In specific embodiments, the solid bridging agent may have a mean particle size in a range of from about 1 micron to about 200 microns, from about 5 microns to about 100 microns, or from about 10 microns to about 50 microns. The solid bridging agent may be present in any suitable amount for a particular application. For example, the solid bridging agent may be present in the water-based drilling fluid in an amount in a range of about 1 wt. % to about 50 wt. % based on a total weight of the drill-in fluid. Alternatively, they may be present in an amount of about 1 wt. % to about 10 wt. % by weight, about 10 wt. % to about 20 wt. % by weight, about 20 wt. % to about 30 wt. % by weight, about 30 wt. % to about 40 wt. % by weight, or about 40 wt. % to about 50 wt. % based on a total weight of the water-based drilling fluid. One of ordinary skill in the art with the benefit of this disclosure should be able to select the appropriate type and amount of solid bridging agent for a particular application.

Water-based drilling fluids may further include additional drilling fluid additives. Any suitable additional additive may be used, including but not limited to, a wetting surfactants, a corrosion inhibitor, a viscosifying agent, a gelling agent, a surfactant, a lost circulation material, a pH control additive, a chelating agent, a scale inhibitor, a gas hydrate inhibitor, and combinations thereof. Suitable viscosifiers may include, but are not limited to, water soluble starches and modified versions thereof, water-soluble polysaccharides and modified versions thereof, water soluble celluloses and modified versions thereof, water soluble polyacrylamides and copolymers thereof, biopolymers, and combinations thereof. One of ordinary skill in the art, with the benefit of this disclosure, should be able to select an appropriate drilling fluid additive for a particular application.

Those of ordinary skill in the art will appreciate that the drilling fluid generally should have a density suitable for a particular application. By way of example, the drilling fluid may have a density in the range of from about 7 pounds per gallon ("lb/gal") (840 kg/m$^3$) to about 20 lb/gal (2400 kg/m$^3$). In certain embodiments, the drilling fluid may have a density in the range of from about 8 lb/gal (960 kg/m$^3$) to about 15 lb/gal (1800 kg/m$^3$) or from about 8.5 lb/gal (1020 kg/m$^3$) to about 12 lb/gal (1440 kg/m$^3$). Those of ordinary skill in the art, with the benefit of this disclosure, should recognize the appropriate density for a particular application.

When drilling a wellbore, the drilling fluid may be continuously circulated from the well surface down to the bottom of the wellbore being drilled and back to the well surface again. As previously described, subterranean formations through which the wellbore may extend may contain shale, which is generally included of various clays. Hydration of the clays, for example, due to exposure to the water-based drilling fluid can be a significant cause of wellbore instability. As described herein, concentration of active clays may be monitored, for example, to determine the efficacy of clay inhibitors in the water-based drilling fluid. Depending on the active clay concentration, additional clay inhibitor may need to be added to the water-based drilling fluid. In accordance with present embodiments, an electric method may be used to monitor active clay content in a drilling fluid and then determine amount of clay inhibitor needed for clay stabilization. The electric method may include, for example, determining methylene blue titration endpoint by using an phase angle measurement of the drilling fluid. In some embodiments, the phase angle may be measured during the methylene blue titration and used in determining the methylene blue titration endpoint.

Embodiments are directed to determining concentration of active clays in water-based drilling fluids. As used herein, the term "active clay" refers to clays that have layers that are negatively charged wherein the layers are kept to together by cations and exhibit the ability to adsorb water between their layers Clays are typically hydrous aluminum silicate minerals that can include, but are not limited to, chlorite, illite, kaolinite, montmorillonite, and smectite. Not all clays in a subterranean formation are considered active clay. However, certain clays may be considered active and can considered active and have a tendency to swell when exposed to water-based drilling fluids. Such clays that are considered active include, but are not limited to, bentonites, and smectites, among others. An example of an active clay includes sodium bentonite. Calcium bentonite is also commonly encountered, but may be considered less active in terms of swelling when compared to sodium bentonite.

The methods and systems disclosed herein may use the methylene blue titration in monitoring concentration of active clays. Methylene blue is a dark green or blue thiazin dye and has a number of uses, one of which is for determining active clay concentration of water-based drilling fluids. Methylene blue may include methylthioninium chloride and water. The methylene blue titration can be used as an indication of the amount of active clays present the water-based drilling fluid based on the methylene blue capacity of the water-based drilling fluid. In the methylene blue titration, methylene blue may be added to a sample of the drilling fluid. Prior to addition, the methylene blue may be treated with hydrogen peroxide and acidified. The methylene blue may be added until saturation is noted by formation of a persistent blue dye "halo" around a drop of solids suspension placed on filter paper. The methylene blue titration may be added, for example, in increments of 0.5 milliliters ("ml"). The methylene blue titration is described in more detail as described in API 13B-1, 4$^{th}$ edition, dated March 2009.

Figure 1:
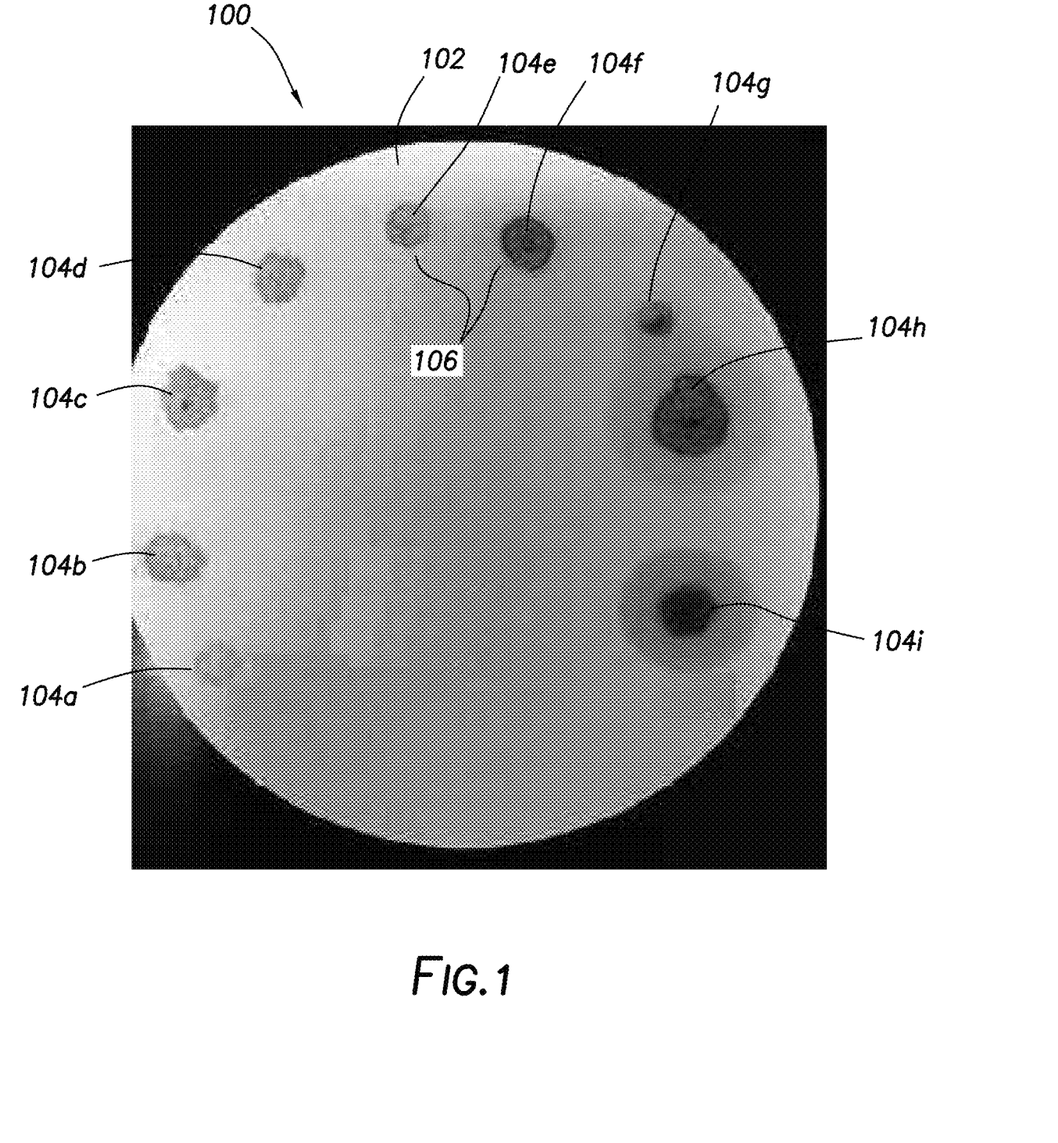
FIG. 1 is an example spot test for endpoint of the methylene blue titration.

FIG. 1 illustrates an example of a spot test for determining the endpoint of the methylene blue titration. The methylene blue titration was performed in accordance with API 13B-1, 4$^{th}$ edition, dated March 2009. In the example, 2 ml of a first water-based drilling fluid was diluted in 50 ml of deionized water. The methylene blue was added into this diluted suspension in increments of 0.5 ml until saturation. The first water-based drilling fluid included a xanthan gum viscosifier, barite, and clay. As seen in FIG. 1, a spot test 100 was performed to determine saturation as noted by formation of a persistent blue dye "halo" around a drop of solids suspension placed on filter paper 102. These drops of the solids suspension are indicated by reference numbers 104a to 104i. The drop 104a corresponds with a 0.5 ml of methylene blue. The drop 104f corresponds with 3 ml of methylene blue. The drop 104i corresponds with 3.5 ml of methylene blue. In addition, consistent blue halos 106 have formed around the drops 104e to 104f, indicating the endpoint is between 2.5 ml and 3 ml. The methylene blue used in this example had a concentration of 3.2 grams per liter ("g/l") (1 ml=0.01 milliequivalents). Thus, the amount of methylene blue used in this test can be directly correlated to the active clay in the first water-based drilling fluid. Using the methylene blue titration, the concentration of the active clay in the first water-based drilling fluid was determined to be approximately 6.25 pounds per barrel (corresponding to 2.5 ml of methylene blue) to 7.5 pounds per barrel (corresponding to 3 ml of methylene blue).

However, as previously noted, while the methylene blue titration has been used in the field, it can time consuming for the titration to proceed to the endpoint, with the potential for system errors impacting the results. Embodiments disclosed herein include determining the endpoint of the methylene blue titration using measurements of phase angle. This endpoint can then be correlated with the active clay contact of the water-based drilling fluid. Any of a variety of suitable techniques may be used for phase angle measurements. Suitable techniques may include, for example, application of an electric field to the sample of the drilling fluid. While the electric field is applied the methylene blue may be added the sample. Measurements of impedance may be made during the addition of the methylene blue. Any suitable electronic equipment may be used for the impedance measurement, including, but not limited to, LCR meters for measuring inductance, capacitance, and resistance. The impedance may be a measured electrical response of the sample to an applied voltage. In some embodiments, the impedance may be the ratio of the complex representation of the sinusoidal voltage to the complex current signal. In some embodiments, the impedance of the sample can be measured over a wide range of frequencies at a fixed voltage. Suitable frequency ranges may include, for example, about 1 Hz to about 10 Mhz, about 20 Hz to about 1 MHz, about 1 Hz to about 500 Hz, or about 1000 Hz to about 10 MHz. In some embodiments, the voltage may be fixed at about at range of, for example, from about 0.2 V to about 2 V, about 0.5 to about 1.5 V. or about 0.8 V to about 1.2 V. In some embodiments, the voltage may be fixed at 1 V. The phase angle may be determined from the impedance measurements. The phase angle has been shown to be sensitive to the addition of methylene blue to the sample of the drilling fluid. While different frequencies may be used, a frequency of about 1 MhZ has shown a significant response to the addition of methylene blue.

Figure 2:
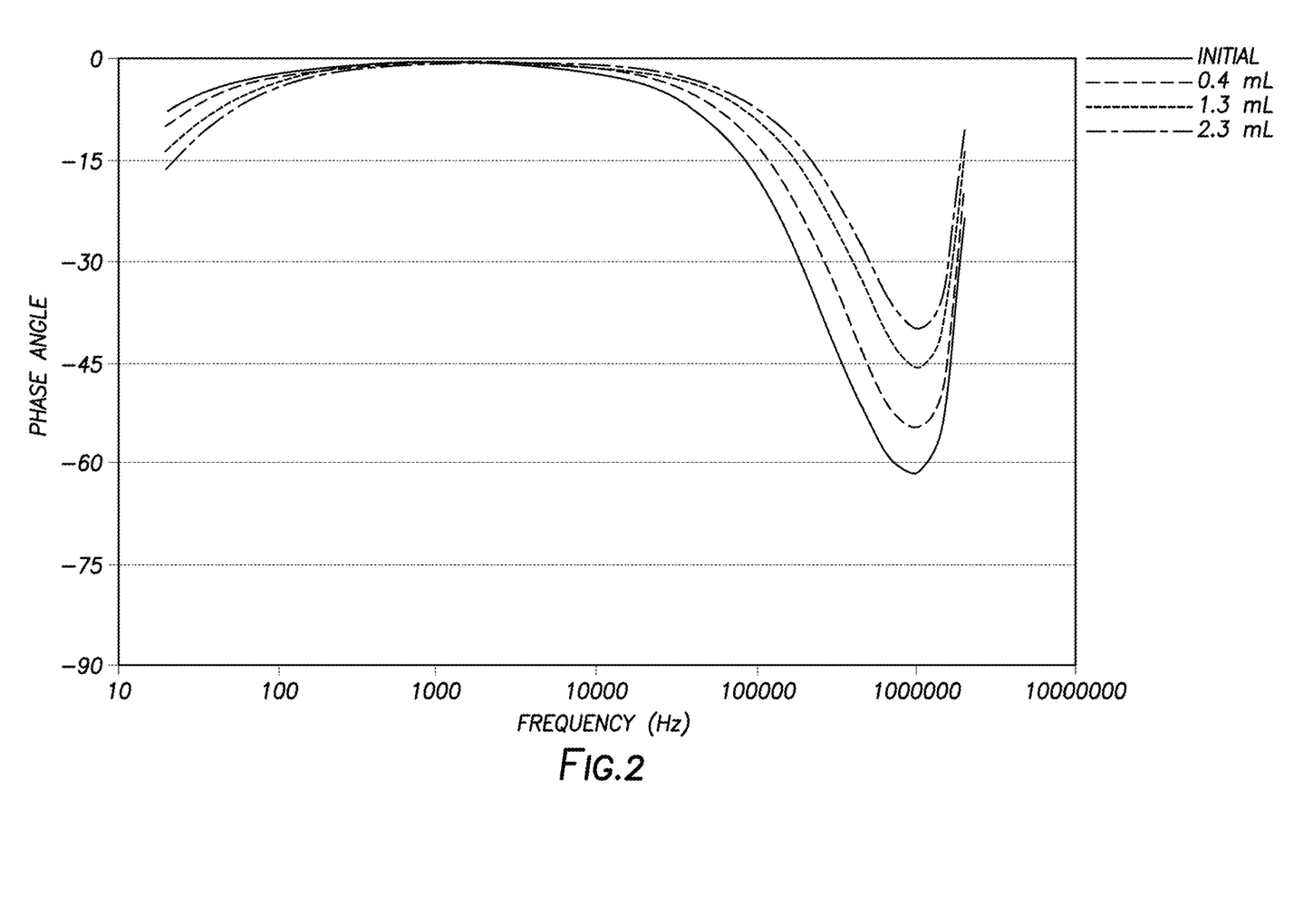
FIG. 2 is an example plot of a phase angle profile for a methylene blue titration on a first water-based drilling fluid.
Figure 3:
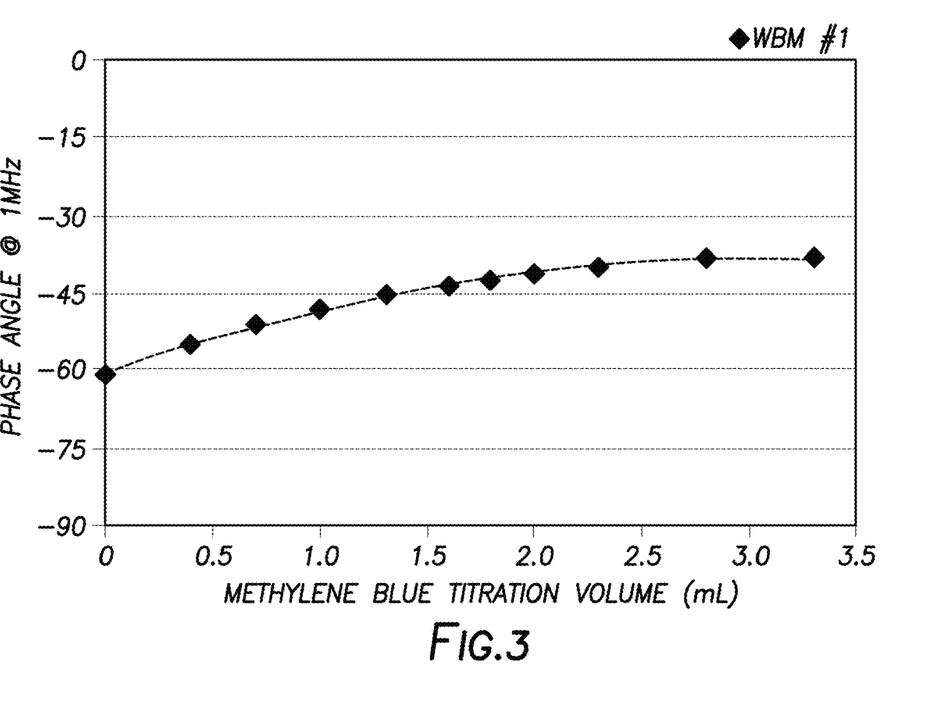
FIG. 3 is an example plot of phase angle at 1 megahertz as a function of methylene blue titration volume for the first water-based drilling fluid.

Sample techniques for determining an endpoint of a methylene blue endpoint will now be discussed in more detail with respect to FIGS. 2-3. For these sample techniques, a methylene blue titration for the water-based drilling fluid was performed while conducting an impedance measurement. The impedance tests were performed over a frequency range of 20 Hz to 1 MHz at a fixed voltage of 1V. THE impedance tests were performed using 1900 Series LCR meter available from QuadTech, Inc. FIG. 2 shows the phase angle profile over the frequency spectrum during the methylene blue titration. As illustrated, the phase angle at 1 MHz shows significant response to the addition of methylene blue. FIG. 3 shows the methylene blue titration volume as a function of phase angle at 1 MHz. The dashed line in FIG. 3 is a polynomial fitting to the experimental data. The plateau of the curve (or derivation of the polynomial function) is an indication of the titration endpoint. It should be understood that term "plateau" as used herein does not necessarily reference a slope of exactly 0, but is intended to reference a region of the curve where the slope is +/−5% of 0. As illustrated by FIG. 3, the titration endpoint is somewhere between 2.5 ml to 3 ml of methylene blue. This result correlates well with the API spot test from FIG. 1, thus indicating that use of phase angle measurements may not require fully titration for determination of endpoint.

Figure 4:
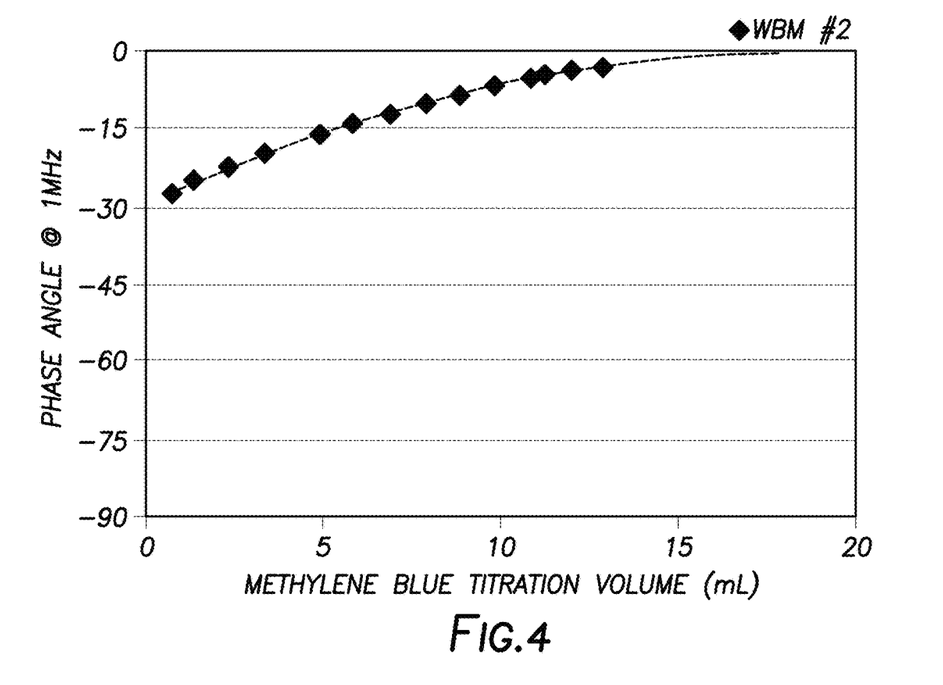
FIG. 4 is an example plot of phase angle at 1 megahertz as a function of methylene blue titration volume for a second water-based drilling fluid.

To further evaluate determination of methylene blue endpoints using impedance measurements, a methylene blue titration for the second water-based drilling fluid was performed while conducting an impedance measurement. The second water-based drilling fluid included xanthan viscosifier, barite, and clay. The second water-based drilling fluid included six times more active clay than the first water-based drilling fluid. FIG. 4 shows the methylene blue titration volume as a function of phase angle at 1 MHz for the second water-based drilling fluid. Although the endpoint was not yet reached, the endpoint can be accurately estimated, for example, from derivation of the polynomial function that fits the experimental data.

In some embodiments, methylene blue titrations with impedance measurements may be used in evaluation of different clay inhibitors. Based on results of monitoring active clay concentration, a recommendation for treatment may then be provided. In some embodiments, the monitoring may be done in real-time, i.e., while the water-based drilling fluid is being circulated in the wellbore. The recommendation for treatment may include, for example, a type and/or concentration of clay inhibitor for addition to the water-based drilling fluid. This is demonstrated in FIGS. 5-8 that follow.

Figure 5:
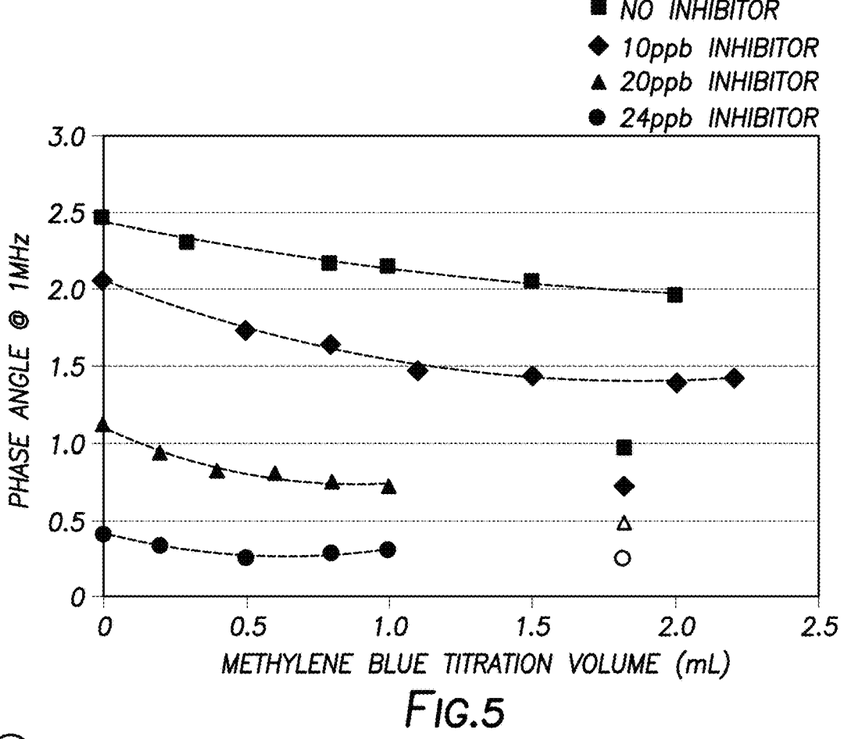
FIG. 5 is an example plot of phase angle at 1 megahertz as a function of methylene blue titration volume for a water-based drilling fluid with different amounts of a first clay inhibitor.
Figure 6:
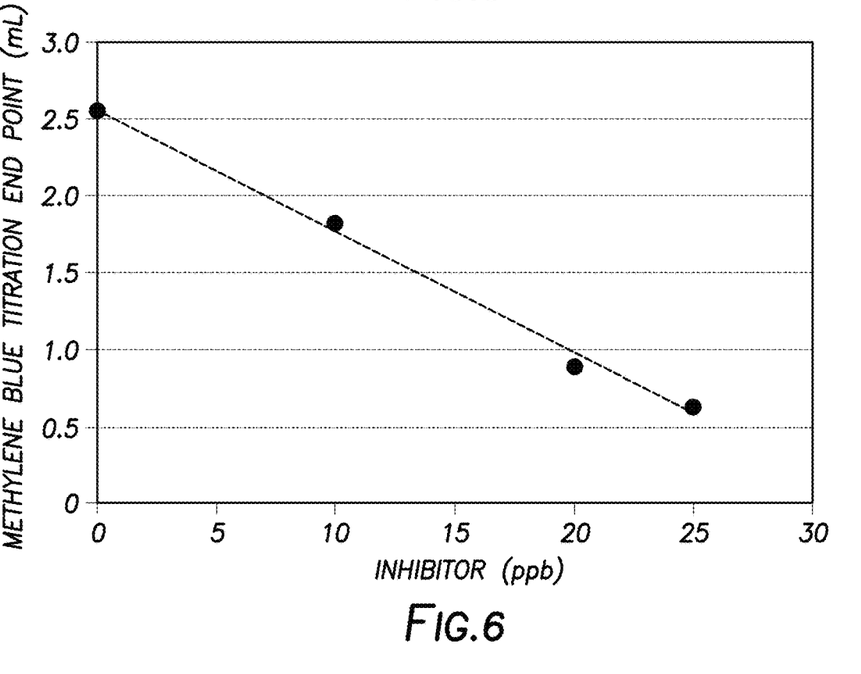
FIG. 6 is an example plot of methylene blue titration endpoint determined from phase angle method as a function of amount of the first clay inhibitor.

FIG. 5 shows additional data for an example technique for a methylene blue titration while conducting an impedance measurement. In FIG. 5, the chart provides phase angle as a function of methylene blue titration volume for the first water-based drilling fluid with different amounts of a first clay inhibitor. The first clay inhibitor is a nonionic polymer. The dashed lines on FIG. 6 are polynomial fitting of the experimental data. As mentioned previously, the endpoint for the methylene blue titration has been calculated by the derivation of the polynomial function that fits the experimental data. In this example, the endpoint is a linear function of the inhibitor amount that is included in the first water-based drilling fluid. In some embodiments, the amount of clay inhibitor may be estimated by the x-axis intercept where the endpoint of the methylene blue titration is zero. In the illustrated example, the approximate amount of clay inhibitor may be estimated to be 32 pounds per barrel of the water-based drilling fluid.

FIG. 6 is a chart of endpoint of the methylene blue titration as a function of inhibitor concentration for the first clay inhibitor. The endpoints were determined using the impedance measurement technique and experimental data for FIG. 5. The correlation provided on FIG. 6 may be used with field testing to determine an amount of the first clay inhibitor to add to the water-based drilling fluid. For example, a sample of the water-based drilling fluid may be taken and the endpoint for methylene blue determined using impedance measurements as previously described. If the endpoint falls below the line shown on FIG. 6, corrective action may be needed by adding additional clay inhibitor. If the endpoint falls above the line, however, sufficient inhibitor concentration is indicated for the current concentration of active clays so no correction action may be needed. In some embodiments, this process can be automated in the drilling system so that the treatment may be recommended in real-time in the drilling system.

Figure 7:
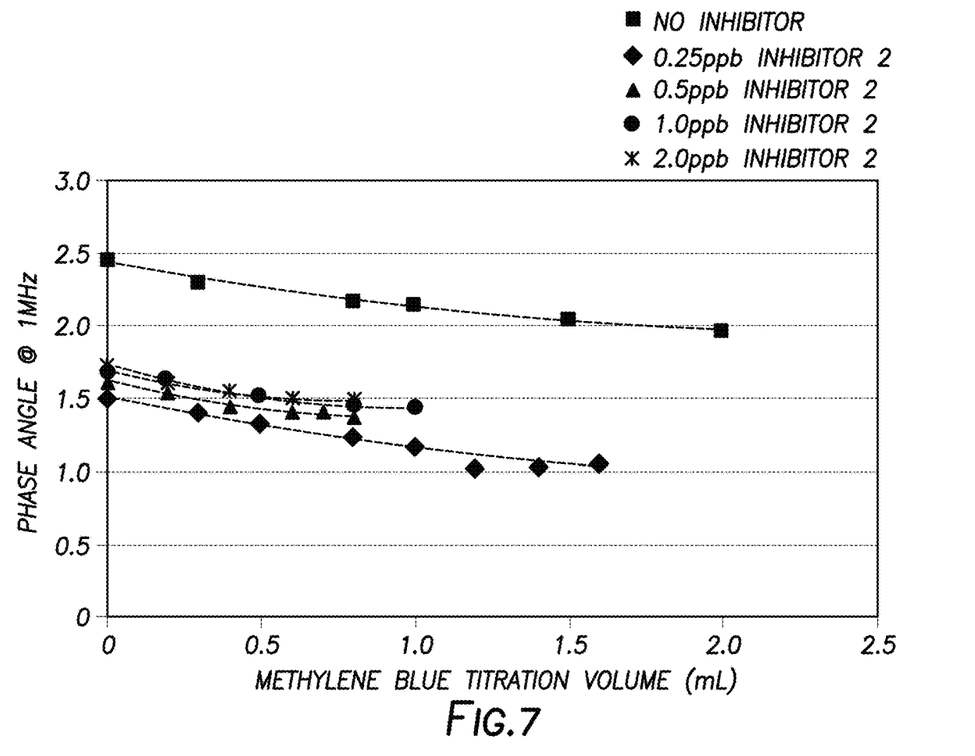
FIG. 7 is an example plot of phase angle at 1 megahertz as a function of methylene blue titration volume for a water-based drilling fluid with different amounts of a second clay inhibitor.
Figure 8:
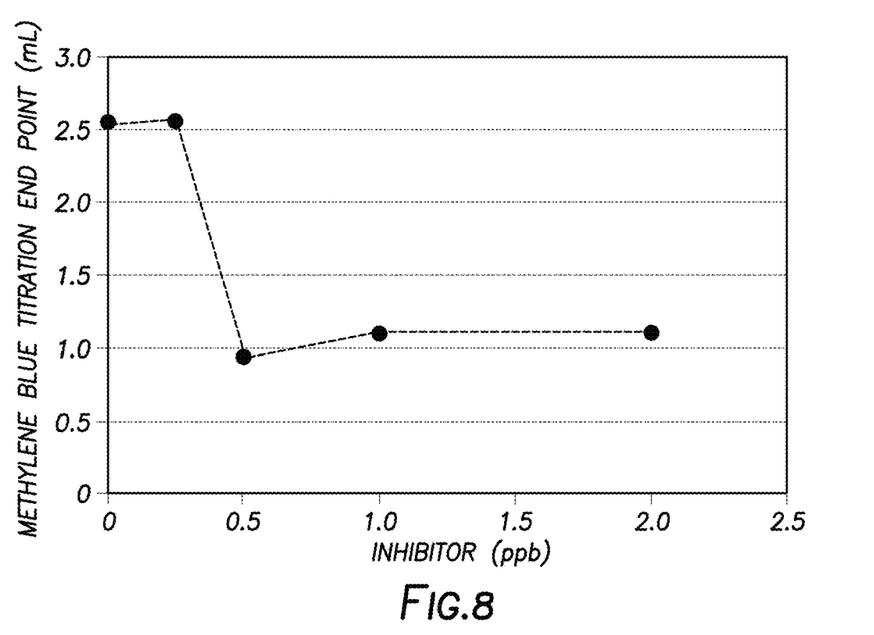
FIG. 8 is an example plot of methylene blue titration endpoint determined from phase angle method as a function of amount of the second clay inhibitor.

Similar example correlations where developed for a second corrosion inhibitor. The second corrosion inhibitor was an anionic polymer. FIG. 7 illustrates the phase angle at 1 MHz as a function of methylene blue titration volume for the first water-based drilling fluid with different amounts of the second inhibitor. The dashed lines are polynomial fittings of the experimental data. Using FIG. 7, the end point of the methylene blue titration may be determined. FIG. 8 is a chart of endpoint of the methylene blue titration as a function of inhibitor concentration for the first clay inhibitor. The dashed lines are polynomial fittings of the experimental data. As illustrated by FIG. 8, the endpoint drops significantly with pounds per barrel of the clay inhibitor, while further increasing the amount of the clay inhibitor does not appear to be beneficial. This could indicate an optical amount of the clay inhibitor.

Figure 9:
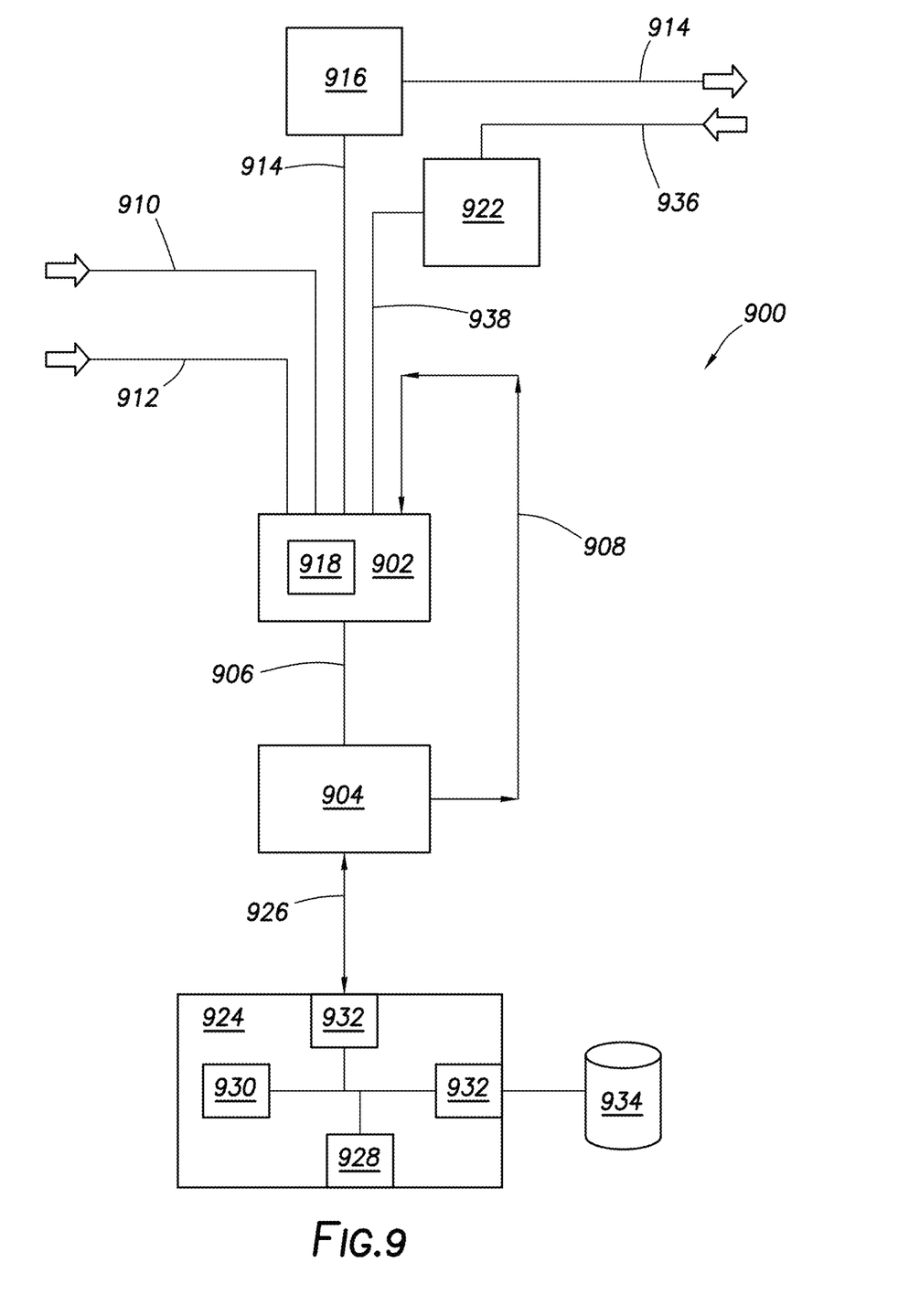
FIG. 9 illustrates a block diagram of a drilling fluid monitoring and handling system.

FIG. 9 illustrates a block diagram of a drilling fluid monitoring and handling system 900. In some embodiments, the drilling fluid monitoring and handling system 900 may be configured to monitor active clay concentration and determine a desired corrective action if needed. For example, the drilling fluid monitoring and handling system 900 may determine an amount of additional clay inhibitor needed in the water-based drilling fluid and automatically add the additional clay inhibitor. As illustrated, the fluid monitoring and handling system 900 may generally include a mud pit 902 and a fluid analysis system 904. The fluid analysis system 904 may be operable to perform a methylene blue titration with an impedance measurement for determination of the endpoint of the methylene blue titration. A sample of the water-based drilling fluid from the mud pit 902 may be fed via a mud pit line 906 to the fluid analysis system 904. The fluid analysis system 904 may analyze the sample of water-based drilling fluid using the example method disclosed above, for example, with respect to FIGS. 2-8. After fluid analysis, the portion of the drilling fluid may be returned to mud pit 902 via a return line 908.

The mud pit 902 may be any vessel suitable for holding a water-based drilling fluid. For example, the mud pit 902 may include a container such as a drum or tank, or a series of containers that may or may not be connected. The mud pit 902 may be supplied with the drilling fluid from an initial drilling fluid supply line 910 that provides an initial supply of water-based drilling fluid to the mud pit 902. However, the initial supply of water-based drilling fluid does not imply that the water-based drilling fluid has not been recycled or circulated in a wellbore, but simply indicates that this supply is not presently being circulated or otherwise used in the wellbore.

Drilling fluid additives (e.g., weighting agents, emulsifying agents, clay inhibitors, clay, viscosifiers, etc.) may be added via a drilling fluid additive supply line 912 to the mud pit 902 (or other suitable location), if desired, and based on the analysis provided by the fluid analysis system 904. Alternatively or additionally, in an example, the results of the analysis may be used to modify the manufacturing process of the water-based drilling fluid. For example, additional clay inhibitor may be added to the water-based drilling fluid in response to the estimated endpoint of the methylene blue titration. After the drilling fluid additives have been added to the water-based drilling fluid, the water-based drilling fluid may be sent to the wellbore for use in drilling operations via a wellbore line 914 by way of mud pump 916.

The mud pit 902 may include a mixing system 918 to mix the contents of the mud pit 902 as well as any drilling fluid additives. For instance, the mixing system 918 may mix the drilling fluid in the mud pit 902 with drilling fluid from the initial drilling fluid supply line 910, drilling fluid from the return line 908, drilling fluid additives, additional non-aqueous fluids, aqueous fluids or combinations thereof. In general, the mixing system 918 may be configured to prevent solids within the drilling fluid from settling. The mixing system 918 may use any suitable mixing technique for mixing of the drilling fluid. For instance, the mixing system 918 may include a static mixer, dynamic mixer, or other suitable mixer. The mud pit 902 may further include suitable pumping equipment (not shown) to pump the drilling fluid in the mud pit 902 to the fluid analysis system 904 via mud pit line 906.

The fluid analysis system 904 may analyze the sample of the drilling fluid in a continuous or non-continuous manner, as desired, and based on whether flow through fluid analysis system 904 is continuous or non-continuous. Although the fluid analysis system 904 is shown at the mud pit 902, examples disclosed herein contemplate the placement of fluid analysis system 904 at any point in the fluid monitoring and handling system 900. For example, fluid analysis system 904 (or a portion thereof) may alternatively be placed in a fluid reconditioning system 922 (discussed below), the mud pit 902, as well as within the wellbore or in an exit conduit from the wellbore. As such, examples disclosed herein contemplate measuring the impedance at any point in the drilling fluid handling process, so that the drilling fluid may be monitored and/or subsequently adjusted as desired.

The analysis performed by fluid analysis system 904 may be performed in collaboration with a computer system 924 communicably coupled thereto. As illustrated, the computer system 924 may be an external component of the fluid analysis system 904, however, the computer system 924 may alternatively include an internal component of the fluid analysis system 904, without departing from the scope of the disclosure. The computer system 924 may be connected to the fluid analysis system 904 via a communication link 926. The communication link 926 may include a direct (wired) connection, a private network, a virtual private network, a local area network, a WAN (e.g., an Internet-based communication system), a wireless communication system (e.g., a satellite communication system, telephones), any combination thereof, or any other suitable communication link.

The computer system 924 may be any suitable data processing system including, but not limited to, a computer, a handheld device, or any other suitable device. The computer system 924 may include a processor 928 and a non-transitory computer readable storage medium 930 communicatively coupled to the processor 928. The processor 928 may include one central processing unit or may be distributed across one or more processors in one or more locations. Examples of a non-transitory computer readable storage medium 930 include random-access memory (RAM) devices, read-only memory (ROM) devices, optical devices (e.g., CDs or DVDs), disk drives, and the like. The non-transitory computer readable storage medium 930 may store computer readable program code that may be executed by the processor 928 to process and analyze the measurement data generated by fluid analysis system 904, adjust the parameters of the fluid monitoring and handling system 900, and/or operate a part or whole of the fluid monitoring and handling system 900. Further, from the impedance measurements together with methylene blue titration information, the water-based drilling fluid measured by the fluid analysis system 904, the program code may be executed by the processor 928 to determine an endpoint of the methylene blue titration and correlate the endpoint with the concentration of active clay in the water-based drilling fluid. Based on the concentration of active clay, the fluid analysis system 904 may a concentration of additional clay inhibitor to add to the water-based drilling fluid.

The computer system 924 may further include one or more input/output ("I/O") interface(s) 932 communicatively coupled to the processor 928. The I/O interface(s) 932 may be any suitable system for connecting the computer system 924 to a communication link, such as a direct connection, a private network, a virtual private network, a local area network, a wide area network ("WAN"), a wireless communication system, or combinations thereof; a storage device, such as storage 934; an external device, such as a keyboard, a monitor, a printer, a voice recognition device, or a mouse; or any other suitable system. The storage 934 may store data required by the fluid analysis system 904 for performing fluid analysis. For instance, the storage 934 may store a collection of equivalent circuit models that may be used during the EIS analysis. The storage 934 may be or include compact disc drives, floppy drives, hard disks, flash memory, solid-state drives, and the like. Those of ordinary skill in the art will appreciate that suitable data processing systems may include additional, fewer, and/or different components than those described for computer system 924.

Data processing and analysis software native to the fluid analysis system 904 and/or installed on the computer system 924 may be used to analyze the data generated by fluid analysis system 904. This procedure may be automated such that the analysis happens without the need for operator input or control. Further, the operator may select from several previously input parameters or may be able to recall previously measured data. Any of the data may be transferred and/or stored on an external memory device (e.g., a USB drive), if desired.

With continued reference to FIG. 9, the drilling fluid may delivered to a wellbore from mud pit 902 by way of mud pump 916 via wellbore line 914. The mud pump 916 may be any type of pump or pumping system useful for circulating a drilling fluid into a subterranean formation under a sufficient pressure. The drilling fluid that has been circulated within the wellbore may be returned to the mud pit 902 via a circulated drilling fluid return line 936 and provided to a fluid reconditioning system 922 to condition the circulated drilling fluid prior to returning it to the mud pit 902. The fluid reconditioning system 922 may be or include one or more of a shaker (e.g., shale shaker), a centrifuge, a hydrocyclone, a separator (including magnetic and electrical separators), a desilter, a desander, a separator, a filter (e.g., diatomaceous earth filters), a heat exchanger, and any fluid reclamation equipment. The fluid reconditioning system 922 may further include one or more sensors, gauges, pumps, compressors, and the like used to monitor, regulate, and/or recondition the drilling fluid and various additives added thereto. After the drilling fluid has been reconditioned, the drilling fluid may be returned to the mud pit 902 via the reconditioned fluid line.

Figure 10:
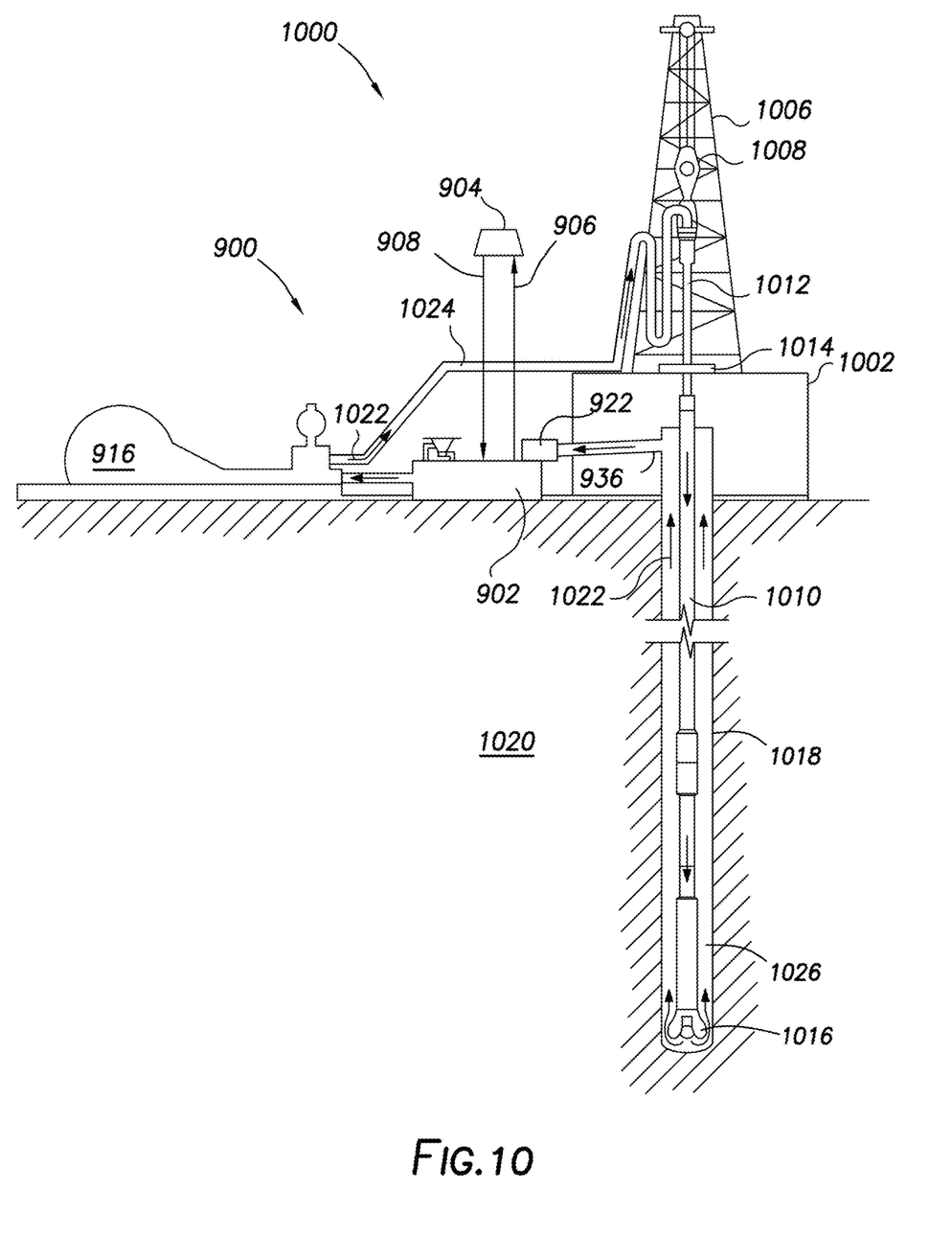
FIG. 10 illustrates an example drilling assembly that incorporates the drilling fluid monitoring and handling system of FIG. 10.

FIG. 10 illustrates an example of a drilling system 1000 that may employ the fluid monitoring and handling system 900 of FIG. 9 described herein to monitor active clay concentration. It should be noted that while FIG. 10 generally depicts a land-based drilling system, those skilled in the art will readily recognize that the principles described herein are equally applicable to subsea drilling operations that employ floating or sea-based platforms and rigs, without departing from the scope of the disclosure.

As illustrated, the drilling system 1000 may include a drilling platform 1002 that supports a derrick 1006 having a traveling block 1008 for raising and lowering a drill string 1010. The drill string 1010 may include, but is not limited to, drill pipe and coiled tubing, as generally known to those skilled in the art. A kelly 1012 may support the drill string 1010 as it may be lowered through a rotary table 1014. A drill bit 1016 may be attached to the distal end of the drill string 1010 and may be driven either by a downhole motor and/or via rotation of the drill string 1010 from the well surface. Without limitation, the drill bit 1016 may include, roller cone bits, PDC bits, natural diamond bits, any hole openers, reamers, coring bits, and the like. As the drill bit 1016 rotates, it may create a wellbore 1018 that penetrates various subterranean formations 1020.

The drilling system 1000 may further include the fluid monitoring and handling system 900 as generally described herein. The mud pump 916 of the fluid monitoring and handling system 900 representatively includes any conduits, pipelines, trucks, tubulars, and/or pipes used to fluidically convey the water-based drilling fluid 1022 downhole, any pumps, compressors, or motors (e.g., topside or downhole) used to drive the water-based drilling fluid 1022 into motion, any valves or related joints used to regulate the pressure or flow rate of the water-based drilling fluid 1022, and any sensors (e.g., pressure, temperature, flow rate, etc.), gauges, and/or combinations thereof, and the like.

The mud pump 916 may circulate may circulate the water-based drilling fluid 1022 through a feed pipe 1024 and to the kelly 1012, which conveys the water-based drilling fluid 1022 downhole through the interior of the drill string 1010 and through one or more orifices in the drill bit 1016. The water-based drilling fluid 1022 may then be circulated back to the surface via an annulus 1026 defined between the drill string 1010 and the walls of the wellbore 1018. At the surface, the recirculated or spent water-based drilling fluid 1022 may be conveyed to the fluid reconditioning system 922 via a circulated drilling fluid return line 936. After passing through the fluid reconditioning system 922, a "cleaned" water-based drilling fluid 1022 may be deposited into a nearby mud pit 902. While illustrated as being arranged at the outlet of the wellbore 1018 via the annulus 1026, those skilled in the art will readily appreciate that the fluid reconditioning system 922 may be arranged at any other location in the drilling system 1000 to facilitate its proper function, without departing from the scope of the scope of the disclosure.

Referring still to FIG. 10, the fluid monitoring and handling system 900 may further include the fluid analysis system 904, which may be disposed on a skid supported on the drilling platform 1002. The fluid analysis system 904 may, for example, continuously or intermittently monitor active clay concentration of the water-based drilling fluid 1022. As illustrated, the water-based drilling fluid 1022 may be taken from the mud pit 902 via the mud pit line 906 and an analyzed drilling fluid may be returned to the mud pit 902 via the return line 908. Alternatively, the active clay concentration may be monitored at fluid reconditioning system 922, or at any other suitable location, even while in the wellbore 1018 if desired.

Thus, the fluid monitoring and handling system 900 may advantageously monitor the concentration of active clay using the example method disclosed herein. The fluid monitoring and handling system 900 may also generate automatic warnings to the personnel when the concentrations deviate from preset safety margins and/or automatically add additional amounts of the clay inhibitor to the drilling fluid when the concentrations deviate from preset safety margins.

Figure 11:
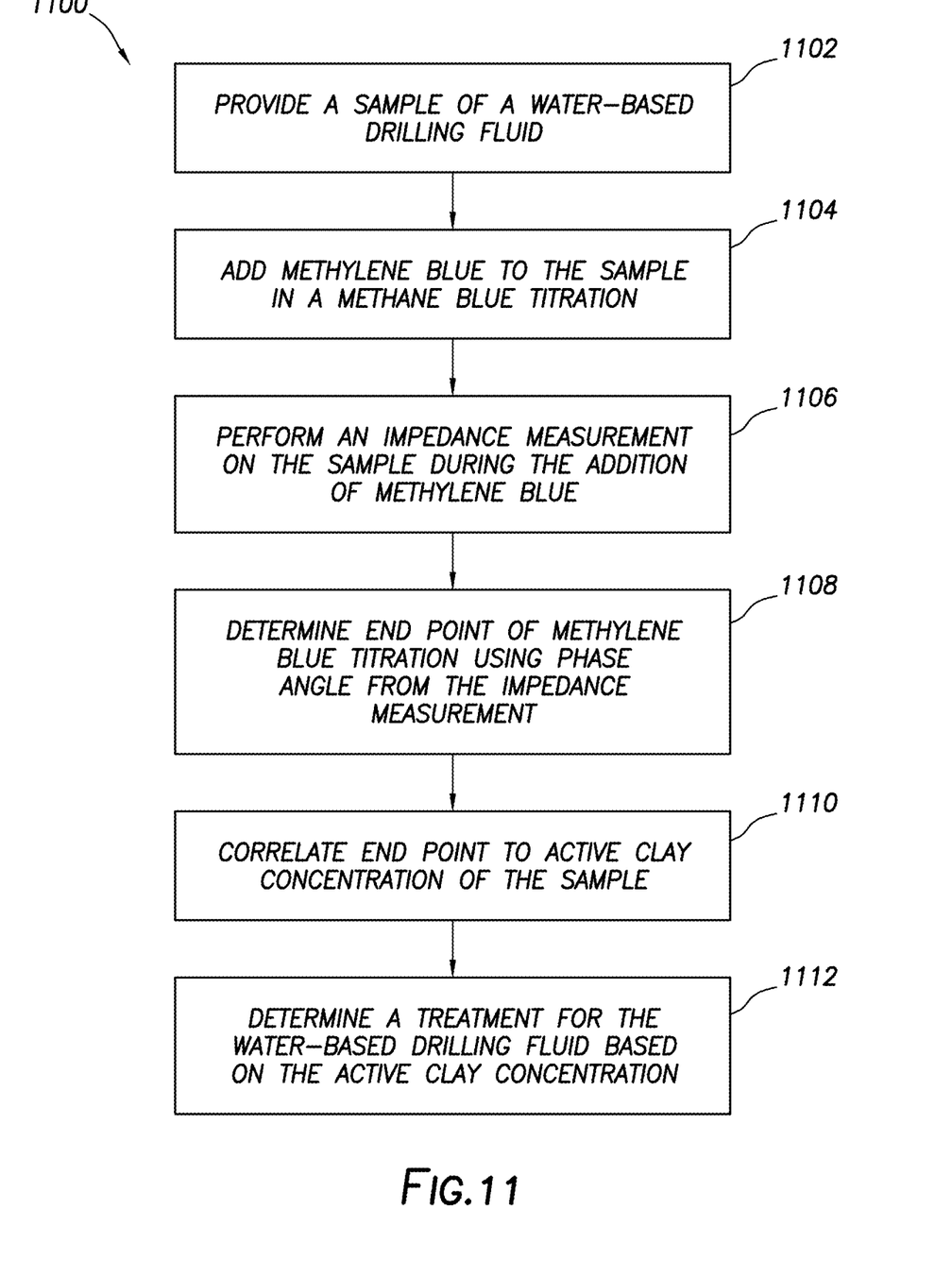
FIG. 11 is a flow chart illustrating an example method for monitoring active clay concentration.

FIG. 11 is a flow chart illustrating an example method 1100 for monitoring active clay concentration. The method 1100 may be implemented, for example, at least partially with fluid monitoring and handling system 900 (e.g., FIG. 9), The method may include obtaining a sample of a water-based drilling fluid, as shown at block 1102. Example compositions of a suitable water-based drilling fluid are described above in the preceding sections. The method 1100 may further include adding methylene blue to the sample of the water-based drilling fluid, as shown at block 1104. Example techniques for methylene blue titration are described above, for example, with respect to FIGS. 1-8, The methylene blue may be added to the sample, for example, in increasing concentrations, for example, in 0.5 ml or 1 ml increments. In some embodiments, before addition of the methylene blue, the sample may be prepared, for example, by addition of hydrogen peroxide and acidified by addition of sulfuric acid. The sample size, preparation, methylene blue addition may be done in accordance with the methylene blue titration described in API 13B-1, $4^{th}$ edition, dated March 2009. However, instead of the spot test, impedance measurements may be used in determining the end point of the methylene blue titration. As illustrated, the method 1100 may further include performing an impedance measurement on the sample while adding the methylene blue, as shown at block 1106. Example techniques for the impedance measurement are described above, for example, with respect to FIGS. 2-8. By way of example, the impedance measurement may be performed at a constant voltage over frequency range. From the impedance measurement, the phase angle may be determined. As described above, the phase angle shows significant response to addition of methylene blue. Accordingly, the method 1100 may further include determining the endpoint of the methylene blue titration using the phase angle from impedance measurement, as shown at block 1108. The endpoint may be determined, for example, based on the plateau of a fitting curve of a graph of phase angle versus methylene blue titration volume. In some embodiments, the fitting curve may be represented as a polynomial function such that derivation of the polynomial function may be used to determine the endpoint. The endpoint corresponds to the volume of methylene added to the sample for saturation. As shown at block 1110, the method 1100 may further include correlating the endpoint to the active clay concentration in the sample of the water-based drilling fluid. The endpoint provides an estimate of the total cation-exchange capacity of the active clay in the sample, which can then be correlated to active clay concentration. One of ordinary skill in the art, with the benefit of this disclosure, should be able to correlate the endpoint of methylene blue titration to active clay concentration. As shown at block 1112, the method 1100 may further include determining a treatment for the water-based drilling fluid based on the active clay concentration. The treatment may include, for example, addition of additional clay inhibitor to the water-based drilling fluid. It may also be determined that the concentration of clay inhibitor is sufficient and no additional clay inhibitor is required.

Figure 12:
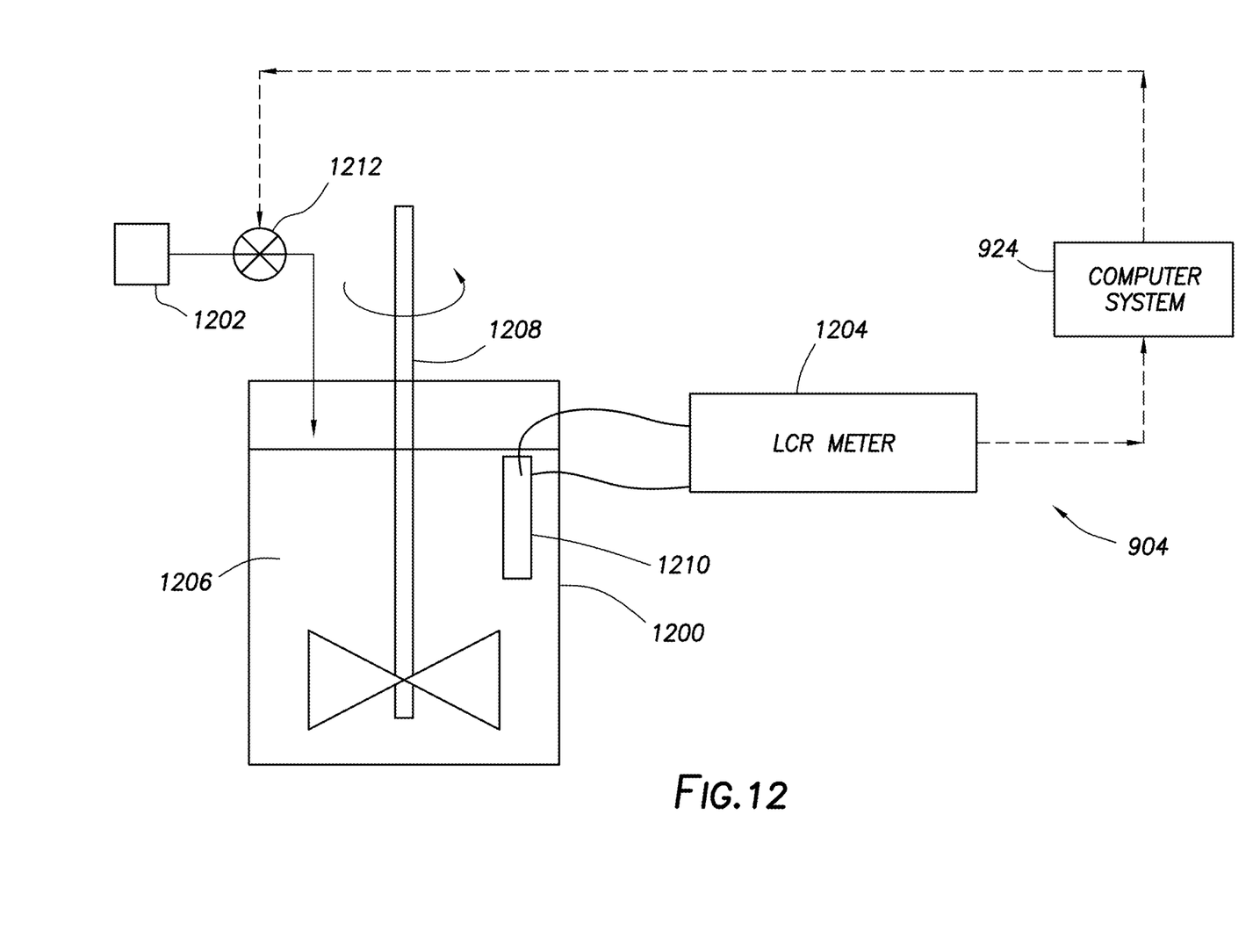
FIG. 12 illustrates an example fluid analysis system for methylene blue titration with impedance measurement.

FIG. 12 illustrates an example configuration of a fluid analysis system 904. By of example, fluid analysis system 904 may be a standalone unit or may be integrated into a fluid handling system 900 as shown on FIGS. 9 and 10. As illustrated, fluid analysis system 904 may include a sample container 1200, a methylene blue container 1202, an LCR meter 1204, and a computer system 924. Sample container 1200 may be any suitable container for holding sample 1206 of a water-based drilling fluid. Agitator 1208 may be disposed in sample 1206 in sample container 1200 for agitating the sample 1206 during analysis. Any suitable type of agitator 1208 may be used, including, but not limited to, paddle agitators, propeller agitators, and helical agitators, among others. LCR meter 1204 may be any suitable electronic equipment for impedance measurement, including, but not limited to, an LCR meter for measuring inductance, capacitance, and resistance. The LCR meter 1204 can measure a number of parameters, including, but not limited, inductance, capacitance, resistance, and phase angle. The LCR meter 1204 may be in signal communication with probe 1210. The LCR meter 1204 may apply an alternating current signal to the probe 1210 with the LCR meter 1204 capturing measurements of the sample 1206 during application of the alternating current signal. By way of example, the LCR meter 1204 may determine inductance, capacitance, resistance, and/or phase angle. In operation, the LCR meter 1204 may be used to obtain these measurements during a methylene blue titration. Methylene blue from methylene blue container 1202 may be added to the sample 1206 in the sample container 1200. By way of example, computer system 924 may send signal to valve 1212 to meter a desired amount of methylene blue into the sample 1206. Computer system 924 may receive the impedance measurements from the LCR meters 1204 and use these impedance measurements for determining the endpoint of the methylene blue titration. Example techniques for determining the endpoint of the methylene blue titration with impedance measurements is described in more detail herein, for example, with respect to FIGS. 1-8.

Accordingly, this disclosure describes systems and methods that are directed to monitoring active clay in water-based drilling fluid. Without limitation, the systems and methods may further be characterized by one or more of the following statements.

Statement 1: A method for monitoring active clay concentration while drilling may be provided. The method may include providing a sample of water-based drilling fluid. The method may further include adding methylene blue to the sample in a methylene blue titration. The method may further include performing an impedance measurement on the sample during the methylene blue titration. The method may further include determining an endpoint of the methylene blue titration using a phase angle measurement from the impedance measurement. The method may further include correlating the endpoint to the active clay concentration of the sample. The method may further include determining a treatment for the water-based drilling fluid based on the active clay concentration.

Statement 2: The method of statement 1, wherein the providing the sample includes feeding the sample from a mud pit containing at least a portion of the water-based drilling fluid to a fluid analysis system fluidically coupled to the mud pit by way of a mud pit line.

Statement 3: The method of statement 1 or 2, wherein the methylene blue includes methylthioninium chloride and water.

Statement 4: The method of any one of statements 1 to 3, wherein the adding the methylene blue includes adding the methylene blue to the sample in increments ranging from about 0.5 milliliters to about 1 milliliter.

Statement 5: The method of any one of statements 1 to 4, further including treating the sample with at least hydrogen peroxide and acidification prior to adding the methylene blue.

Statement 6: The method of any one of statements 1 to 4, wherein the impedance measurement is performed at constant voltage over a frequency range.

Statement 7: The method of statement 6, wherein the frequency range is from about 20 Hz to about 1 MHz.

Statement 8: The method of any one of statements 1 to 7, wherein the determining the endpoint includes deriving a polynomial function for phase angle as a function of methylene blue titration volume.

Statement 9: The method of statement 8, wherein the phase angle for the polynomial function is at a frequency of about 1 MHz.

Statement 10: The method of any one of statements 1 to 9, the determining the treatment includes determining an amount of clay inhibitor to add to the water-based drilling fluid.

Statement 11: The method of any one of statements 1 to 10, further including adding clay inhibitor to the water-based drilling fluid in response to the determined treatment.

Statement 12: The method of statement 1, wherein the method further includes circulating the water-based drilling fluid through a wellbore while drilling in the wellbore to extend the wellbore; wherein the providing the sample includes feeding the sample a mud pit containing the water-based drilling fluid to a fluid analysis system fluidically coupled to the mud pit by way of a mud pit line; wherein the adding the methylene blue includes adding the methylene blue to the sample in increments ranging from about 0.5 milliliters to about 1 milliliter; wherein the impedance measurement is performed at constant voltage over a frequency range of from about 20 Hz to about 1 MHz; wherein the determining the endpoint includes deriving a polynomial function for phase angle at about 1 MHz as a function of methylene blue titration volume; and wherein the method further includes adding clay inhibitor to the water-based drilling fluid in response to the determined treatment.

Statement 13: The method of any one of statements 1 to 12, further including sending a signal from a computer system to add clay inhibitor to the drilling fluid in response to the determined treatment.

Statement 14: A drilling method may be provided that includes circulating a water-based drilling fluid through a wellbore while drilling the wellbore. The drilling method may further include adding methylene blue to a sample of the water-based drilling fluid in a methylene blue titration while performing an impedance measurement in real-time while the water-based drilling fluid is circulated in the well bore. The drilling method may further include determining an endpoint of the methylene blue titration using a phase angle measurement from the impedance measurement. The drilling method may further include adding clay inhibitor to the water-based drilling fluid based at least partially on the endpoint of the methylene blue titration.

Statement 15: The method of statement 14, further including feeding the sample from a mud pit containing at least a portion of the water-based drilling fluid to a fluid analysis system fluidically coupled to the mud pit by way of a mud pit line.

Statement 16: The method of claim 15, wherein the fluid analysis system sends signals to initiate the adding the methylene blue and the adding the clay inhibitor, and wherein the fluid analysis system determines the endpoint.

Statement 17: The method of any one of statements 14 to 16, wherein the impedance measurement is performed at a constant voltage over a frequency range of about 20 Hz to about 1 MHz.

Statement 18: The method of any one of statements 14 to 17, wherein the determining the endpoint includes deriving a polynomial function for phase angle as a function of methylene blue titration volume.

Statement 19: A drilling system may be provided that includes a drill string. The drilling system may further include a drill bit attached to a distal end of the drill string. The drilling system may further include a fluid monitoring and handling system. The fluid monitoring and handling system may include a mud pit operable to receive a water-based drilling fluid from a wellbore. The fluid monitoring and handling system may include a mud pump operable to circulate the water-based drilling fluid. The fluid monitoring and handling system may include a fluid analysis system including a sample container for a sample of water-based drilling fluid, an LCR meter for measuring impedance of the sample, and a methylene blue container including methylene blue. The fluid monitoring and handling system may include a computer system in signal communication with the fluid analysis system, wherein the computer system includes a processor and a non-transitory computer readable storage medium that when executed by the processor causes the computer system to send a first signal to initiate a methylene blue titration on the sample, send a second signal to initiate an impedance measurement while adding the methylene blue, and estimate an endpoint of the methylene blue titration using the impedance measurement.

Statement 20: The drilling system of statement 19, wherein the non-transitory computer readable storage medium further causes the computer system to send a third signal to cause addition of clay inhibitor to the water-based drilling fluid based at least partially on the endpoint.

The preceding description provides various embodiments of the systems and methods of use disclosed herein which may contain different method steps and alternative combinations of components. It should be understood that, although individual embodiments may be discussed herein, the present disclosure covers all combinations of the disclosed embodiments, including, without limitation, the different component combinations, method step combinations, and properties of the system. It should be understood that the compositions and methods are described in terms of "including," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present embodiments are well adapted to attain the ends and advantages mentioned as well as those that are inherent therein. The particular embodiments disclosed above are illustrative only, and may be modified and practiced in different but equivalent manners apparent to those skilled in the art having the benefit of the teachings herein. Although individual embodiments are discussed, the disclosure covers all combinations of all of the embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of those embodiments. If there is any conflict in the usages of a word or term in this specification and one or more patent(s) or other documents that may be incorporated herein by reference, the definitions that are consistent with this specification should be adopted.

What is claimed is:

1. A method for monitoring active clay concentration while drilling, comprising:

providing a sample of water-based drilling fluid;
adding methylene blue to the sample in a methylene blue titration;
performing an impedance measurement on the sample during the methylene blue titration;
determining an endpoint of the methylene blue titration using a phase angle measurement from the impedance measurement;
correlating the endpoint to the active clay concentration of the sample; and
determining a treatment for the water-based drilling fluid based on the active clay concentration.

2. The method of claim 1, wherein the providing the sample comprises feeding the sample from a mud pit containing at least a portion of the water-based drilling fluid to a fluid analysis system fluidically coupled to the mud pit by way of a mud pit line.

3. The method of claim 1, wherein the methylene blue comprises methylthioninium chloride and water.

4. The method of claim 1, wherein the adding the methylene blue comprises adding the methylene blue to the sample in increments ranging from about 0.5 milliliters to about 1 milliliter.

5. The method of claim 1, further comprising treating the sample with at least hydrogen peroxide and acidification prior to adding the methylene blue.

6. The method of claim 1, the determining the treatment comprises determining an amount of clay inhibitor to add to the water-based drilling fluid.

7. The method claim 1, further comprising adding clay inhibitor to the water-based drilling fluid in response to the determined treatment.

8. The method of claim 1:
wherein the method further comprises circulating the water-based drilling fluid through a wellbore while drilling in the wellbore to extend the wellbore;
wherein the providing the sample comprises feeding the sample a mud pit containing the water-based drilling fluid to a fluid analysis system fluidically coupled to the mud pit by way of a mud pit line;
wherein the adding the methylene blue comprises adding the methylene blue to the sample in increments ranging from about 0.5 milliliters to about 1 milliliter;
wherein the impedance measurement is performed at constant voltage over a frequency range of from about 20 Hz to about 1 MHz;
wherein the determining the endpoint comprises deriving a polynomial function for phase angle at about 1 MHz as a function of methylene blue titration volume; and
wherein the method further comprises adding clay inhibitor to the water-based drilling fluid in response to the determined treatment.

9. The method of claim 1, further comprising sending a signal from a computer system to add clay inhibitor to the drilling fluid in response to the determined treatment.

10. The method of claim 1, wherein the impedance measurement is performed at constant voltage over a frequency range.

11. The method of claim 10, wherein the frequency range is from about 20 Hz to about 1 MHz.

12. The method of claim 1, wherein the determining the endpoint comprises deriving a polynomial function for phase angle as a function of methylene blue titration volume.

13. The method of claim 12, wherein the phase angle for the polynomial function is at a frequency of about 1 MHz.

14. A drilling method, comprising:
circulating a water-based drilling fluid through a wellbore while drill wellbore
adding methylene blue to a sample of the water-based drilling fluid in a methylene blue titration while performing an impedance measurement in real-time while the water-based drilling fluid is circulated in the well bore;
determining an endpoint of the methylene blue titration using a phase angle measurement from the impedance measurement; and
adding clay inhibitor to the water-based drilling fluid based at least partially on the endpoint of the methylene blue titration.

15. The method of claim 14, wherein the impedance measurement is performed at a constant voltage over a frequency range of about 20 Hz to about 1 MHz.

16. The method of claim 14, wherein the determining the endpoint comprises deriving a polynomial function for phase angle as a function of methylene blue titration volume.

17. The method of claim 14, further comprising feeding the sample from a mud pit containing at least a portion of the water-based drilling fluid to a fluid analysis system fluidically coupled to the mud pit by way of a mud pit line.

18. The method of claim 17, wherein the fluid analysis system sends signals to initiate the adding the methylene blue and the adding the clay inhibitor, and wherein the fluid analysis system determines the endpoint.

19. A drilling system comprising:
a drill string;
a drill bit attached to a distal end of the drill string;
a fluid monitoring and handling system comprising
a mud pit operable to receive a water-based drilling fluid from a wellbore;
a mud pump operable to circulate the water-based drilling fluid; and
a fluid analysis system comprising a sample container for a sample of water-based drilling fluid, an LCR meter for measuring impedance of the sample, and a methylene blue container comprising methylene blue; and
a computer system in signal communication with the fluid analysis system, wherein the computer system comprises a processor and a non-transitory computer readable storage medium that when executed by the processor causes the computer system to send a first signal to initiate a methylene blue titration on the sample, send a second signal to initiate an impedance measurement while adding the methylene blue, and estimate an endpoint of the methylene blue titration using the impedance measurement.

20. The drilling system of claim 19, wherein the non-transitory computer readable storage medium further causes the computer system to send a third signal to cause addition of clay inhibitor to the water-based drilling fluid based at least partially on the endpoint.

* * * * *